US006752849B2

(12) United States Patent
Logan et al.

(10) Patent No.: US 6,752,849 B2
(45) Date of Patent: Jun. 22, 2004

(54) METHOD FOR DISINFECTING AND STABILIZING ORGANIC WASTES WITH MINERAL BY-PRODUCTS

(75) Inventors: Terry J. Logan, Columbus, OH (US); Ervin L. Faulmann, Toledo, OH (US)

(73) Assignee: N-Viro International Corporation, Toledo, OH (US)

( * ) Notice: Subject to any disclaimer, the term of this patent is extended or adjusted under 35 U.S.C. 154(b) by 0 days.

(21) Appl. No.: 10/298,958

(22) Filed: Nov. 19, 2002

(65) Prior Publication Data

US 2003/0136165 A1 Jul. 24, 2003

Related U.S. Application Data

(63) Continuation-in-part of application No. 09/923,531, filed on Aug. 8, 2001.

(51) Int. Cl.⁷ .................................................. C05F 3/00
(52) U.S. Cl. ..................... 71/11; 71/12; 71/13; 71/14; 71/15; 71/23; 71/25; 71/29
(58) Field of Search .............................. 71/11, 12, 13, 71/14, 15, 23, 25, 29

(56) References Cited

U.S. PATENT DOCUMENTS

| | | | |
|---|---|---|---|
| 3,476,683 A | 11/1969 | Liljegren | 210/8 |
| 3,877,920 A | 4/1975 | Carlberg | 71/21 |
| 4,079,003 A | 3/1978 | Manchak | 210/46 |
| 4,143,122 A | 3/1979 | Laufhütte | 423/574 R |
| 4,159,682 A | 7/1979 | Fitch et al. | 110/245 |
| 4,255,129 A | 3/1981 | Reed et al. | 432/13 |
| 4,532,873 A | 8/1985 | Rivers et al. | 110/347 |
| 4,554,002 A | 11/1985 | Nicholson | 71/12 |
| 4,781,842 A | 11/1988 | Nicholson | 210/751 |
| 4,787,323 A | 11/1988 | Beer et al. | 110/346 |
| 4,902,431 A | 2/1990 | Nicholson et al. | 210/751 |
| 4,946,382 A | 8/1990 | Kobayashi et al. | 431/8 |
| 4,970,803 A | 11/1990 | Keller | 34/10 |
| 4,997,572 A | 3/1991 | Wurtz | 210/710 |
| 5,135,664 A | 8/1992 | Burnham | 210/751 |
| 5,196,043 A | 3/1993 | Wurtz | 71/12 |
| 5,211,723 A | 5/1993 | Khan et al. | 48/197 R |
| 5,229,011 A | 7/1993 | Christy, Sr. et al. | 210/751 |
| 5,275,733 A | 1/1994 | Burnham | 210/609 |
| 5,277,826 A | 1/1994 | Burns et al. | 210/751 |
| 5,307,765 A | 5/1994 | Virr | 122/4 D |
| 5,346,616 A | 9/1994 | Christy, Sr. et al. | 210/179 |
| 5,417,861 A | 5/1995 | Burnham | 210/609 |
| 5,422,015 A | 6/1995 | Angell et al. | 210/751 |
| 5,490,907 A | 2/1996 | Weinwurm et al. | 203/29 |
| 5,525,239 A | 6/1996 | Duske | 210/739 |
| 5,741,346 A * | 4/1998 | Glover | 71/15 |
| 5,746,006 A | 5/1998 | Duske et al. | 34/136 |
| 5,837,142 A | 11/1998 | Mullerheim et al. | 210/650 |
| 5,849,050 A | 12/1998 | Wolf | 48/197 R |
| 5,853,590 A | 12/1998 | Burnham | 210/609 |
| 5,937,770 A | 8/1999 | Kobayashi et al. | 110/263 |
| 6,048,510 A | 4/2000 | Zauderer | 423/235 |
| 6,056,880 A | 5/2000 | Boss et al. | 210/695 |
| 6,234,093 B1 | 5/2001 | Finker et al. | 110/266 |
| 6,237,246 B1 | 5/2001 | Millard | 34/343 |
| 6,248,148 B1 | 6/2001 | Faulmann et al. | 71/11 |
| 6,298,796 B1 | 10/2001 | Okazaki et al. | 110/345 |
| 6,402,801 B1 | 6/2002 | Faulmann et al. | 71/11 |
| 6,405,664 B1 | 6/2002 | Logan et al. | 110/345 |

FOREIGN PATENT DOCUMENTS

JP          03059303 A      3/1991    ........... F23C/11/00

OTHER PUBLICATIONS

*Alkaline Reagents in the N–Viro Process and Effects on N–Viro Soil*, N–Viro Soil Research and Experience on Product Use 8, pp. 1–2 (1996).

M. McCoy, *Cleaning up the air with chemicals*, C&EN Northwest News Bureau, pp. 35, 36, 38 (2001).

\* cited by examiner

*Primary Examiner*—C. Sayala
(74) *Attorney, Agent, or Firm*—Kenyon & Kenyon (57) ABSTRACT

Disclosed is a method of disinfecting and stabilizing organic wastes wherein organic waste is intimately mixed with one or more mineral by-products to produce a mixture having a pH of less than about 9. The mixture is heated and dried to produce a stable, granular bio-mineral product that may be used for example, as a fertilizer, soil amendment or as a soil substitute. In some embodiments, at least a portion of the heat for heating and/or drying the mixture is provided by residual heat in at least one of the one or more mineral by-products. Also provided are stable, granular bio-mineral products formed by the methods of the present invention and fertilizers, soil amendments, and soil substitutes that include these stable, granular bio-mineral products. Further provided are systems for disinfecting and stabilizing organic waste, and systems for making a stable, granular bio-mineral product.

24 Claims, 3 Drawing Sheets

METHOD FOR DISINFECTING AND STABILIZING ORGANIC WASTES WITH MINERAL BY-PRODUCTS

This application is a continuation-in-part of application Ser. No. 09/923,531, filed Aug. 8, 2001, the contents of which are incorporated herein in their entirety.

FIELD OF THE INVENTION

The present invention relates to methods of disinfecting and stabilizing organic waste so as to produce a stable, granular bio-mineral product, which has reduced levels of harmful pathogens. The methods include intimately mixing organic waste with one or more mineral by-products to form a mixture having a pH less than about 9, and heating and drying the mixture to produce a stable, granular bio-mineral product. Suitable mineral by-products according to the present invention include those that will result in the mixture having a pH below about 9, thereby minimizing the production of odor-causing gases, such as ammonia and methyl amines from the organic waste.

The present invention also relates to a stable, granular bio-mineral product produced by these methods. The invention further relates to fertilizers, soil amendments and soil substitutes that include these stable, granular bio-mineral products.

BACKGROUND OF THE INVENTION

Various techniques have been developed for the purpose of sterilizing or decontaminating biological sludges and wastes. In 1993 the U.S. Environmental Protection Agency promulgated rules for the treatment and management of municipal sewage sludge (EPA, 1993). These rules set standards for pathogen destruction (disinfection), vector attraction reduction (VAR), and metal contaminant reduction in sewage sludge. The disinfection standards are separated into two categories, Class B in which sludges are treated to partially destroy pathogens, and Class A where pathogenic bacteria, enteric viruses and helminth parasites are reduced to near detection limits.

Processes previously approved by EPA as Class A disinfection processes include: thermal treatment, based on a prescribed time-temperature relationship; advanced alkaline stabilization with accelerated drying, combining raising a pH above 12 for 72 hours, heating to greater than 52° C. for 12 hours, and producing solids greater than 50%; composting; heat drying; heat treatment of liquid sludge; thermophilic aerobic digestion; beta ray irradiation; gamma ray irradiation; pasteurization (temperature greater than 70° C. for at least 30 minutes); a combination of a pH reaching at least 12 and pasteurization; and several advanced digestion processes (EPA, 1999).

These disinfection processes may be classified as follows: (1) heat; (2) high pH (reaching a pH over 11 or 12 during the process); (3) digestion; (4) irradiation; or (5) drying processes, or a combination of one or more of these processes.

Heating to a sufficient temperature for a proscribed period of time is an effective disinfectant method, and complete sterilization may be achieved at temperatures below 100° C. for a few minutes. The U.S. Environmental Protection Agency established a sliding time-temperature scale based on the equation:

$$D = 131{,}700{,}000/10^{0.1400t}$$

where D=days and t=temperature (° C.) (EPA, 1999), in one of its methods of achieving Class A disinfection.

Because temperature is the sole disinfectant under this alternative, the EPA has required that the process demonstrate that every particle of sludge be exposed to the required temperature for the required time.

The use of chemical additives such as acids, alkalis, and combinations of acids and alkalis with electric heat or heated air to disinfect by heating has been described, for example, in U.S. Pat. Nos. 4,079,003; 4,902,431; 5,196,043; 5,346,616; 5,422,015; 5,525,239; 5,746,006; 5,853,590 and 6,056,880. These methods rely exclusively on high heat (185° F.) for disinfection. They are disadvantageous in that the high temperature is high enough for long enough to destroy most if not all beneficial microorganisms. The use of direct and indirect dryers to dry materials such as sewage sludge is known.

The importance of achieving disinfection at the lowest possible temperatures so as to preserve viable populations of non-pathogenic microorganisms and thereby enhance product stability has also been described, for example, in U.S. Pat. Nos. 4,781,842; 4,902,431; 5,135,664; 5,275,733; and 5,417,861.

Examples of Class A disinfection processes relating to high pH (that is, reaching a pH of 12 or higher at some point in the process) as a specific disinfectant are set forth, for example, in U.S. Pat. Nos. 3,476,683; 4,079,003; 4,554,002; 4,781,842; 4,902,431; 4,997,572; 5,135,664; 5,196,043; 5,229,011; 5,277,826; 5,853,590. Although high pH is a proven disinfectant, a high pH product has problems associated with odor-causing gaseous emissions due to alkaline reactions with the sludge. Among the noxious gases are ammonia and di- and trimethyl amines.

A traditional method of stabilizing organic wastes against odor generation and attraction of disease vectors such as flies, is to add alkali and raise pH between 11 and 12. EPA recognizes high pH as a means of achieving VAR under 40 C.F.R. part 503 (EPA, 1999). In this method, the sludge pH must be held at pH 12 for 2 hours and subsequently at pH 11.5 for 22 hours. This is a temporary stabilization process if insufficient alkali is added to maintain the pH of the sludge until it can be incorporated into the soil. Likewise, EPA recognizes VAR by high solids but this form of stabilization alone is inadequate if the material is wetted.

The art has used mineral by-products in stabilizing semi-solid, odorous organic wastes through bulk drying, odor absorption, and granulation, see for example, U.S. Pat. Nos. 3,877,920 and 4,554,002. Mineral materials including sand, diatomaceous earth, perlite, and various mineral reagent powders have been used in conjunction with fluidized heating, drying and burning of sludges and oily wastes. See for example, U.S. Pat. Nos. 4,159,682, 4,787,323, 4,970,803, 5,490,907.

Burnham and Striebig have disclosed a method to combine acid, alkali and external heat to pasteurize and chemically modify sewage sludge. The purpose of the acid and alkali addition in these methods is to adjust pH to a desirable range (i.e., over 12). No by-products are used in these processes, only virgin acid and agricultural limestone.

Digestion methods, which are well known in the art, are only applicable to liquid wastes. Digestion is also disadvantageous because the digestion process is susceptible to disturbances of flow, nutrient loadings, temperature, chemical content, accumulated sludge levels and other influences; digestion requires long retention times in large tanks; and close supervision of the process by skilled operators is often required for acceptable performance, although such supervision is no guarantee of a good outcome.

Irradiation methods disinfect by directly destroying pathogen cells. These methods are not used in practice.

An efficient method of disinfecting and stabilizing organic waste without destroying beneficial microorganisms, as in previously known heating methods, is desirable. Additionally, a method resulting in a product that does not produce significant amounts of noxious odors caused by the products of known high pH methods is also desirable.

SUMMARY OF THE INVENTION

The present invention relates to methods of disinfecting and stabilizing organic wastes by intimately mixing organic waste with mineral by-products, and heating and drying the bio-mineral mixture having a pH of less than about 9. The one or more mineral by-products preferably include a mineral by-product having a pH of less than about 9 or a mixture of mineral by-products having a combined pH of less than about 9. The present methods are advantageous over previous methods in that they are efficient, permit the survival of beneficial microorganisms and provide a product that is granular, relatively free of high pH-causing odors, stable, and may be used as a fertilizer, soil amendment or soil substitute.

The present invention also relates to stable, granular bio-mineral products produced by the methods described herein and to fertilizers, soil amendments and soil substitutes that include these stable, granular bio-mineral products.

The present invention further relates to systems for disinfecting and stabilizing organic waste and for making a stable, granular bio-mineral product. These systems include a means for intimately mixing organic waste and one or more mineral by-products, where the mixture has a pH less than about 9. The systems further include heating means and drying means to heat and dry the mixture.

In some embodiments of the present invention, at least a portion of the heat for heating, drying, disinfecting and/or stabilizing the mixture of organic waste and mineral by-product(s) is provided by residual heat in hot fly ash or other hot mineral by-products.

DETAILED DESCRIPTION

The present invention will now be described in detail for specific preferred embodiments of the invention, it being understood that these embodiments are intended only as illustrative examples and the invention is not to be limited thereto.

The present invention relates to the field of waste management, and in particular to methods of disinfecting and stabilizing organic wastes. The present inventors have discovered the effect of mineral by-products, combined with heating and thermal drying, under non-alkaline conditions, on the stability, in particular biological stability, of the organic waste. Accordingly, the present invention relates to methods of disinfecting and stabilizing organic wastes, which include intimately mixing organic wastes with one or more mineral by-products, and drying and heating the organic wastes and mineral by-products to produce granular bio-mineral products. The methods of the present invention result in stable, bio-mineral products that are preferably granular and dry, which may be utilized as a macro and micro nutrient fertilizer, soil amendment and soil substitute.

The present invention is advantageous over the prior art in that it allows for thermal disinfection at lower time-temperature combinations than required by previously known methods. The present methods are also more efficient than prior processes because shorter processing periods reduce capital costs and space requirements by increasing throughput. The lower disinfection temperatures of the present invention allows for the survival of non-pathogenic microorganisms such as non-pathogenic microflora, helps to reduce gaseous emissions, and increases product stability.

The mineral by-product(s) of the present invention are selected such that they result in the mixture of organic waste and mineral by-products having a pH of less than about 9. The mineral by-product(s) preferably include a mineral by-product having a pH of less than about 9 or a mixture of mineral by-products having a combined pH of less than about 9. The mixture of organic waste and mineral by-products preferably maintains a pH of less than about 9 throughout heating and drying. Most preferably, the pH is maintained between about 7 and about 9 throughout the entire method.

The present methods are advantageous over those methods in the art, which reached a high pH (i.e., over 9.5) in that by maintaining the mixture at a pH below 9 throughout the method, production of noxious gases, from ammonia and methyl amines for example, is reduced as compared to prior methods. Products produced by these methods also have this advantage in that they do not produce significant noxious odors or significant amounts of ammonia or methyl amines, when rewet. Significant noxious odors means that the odor level is objectionable. Therefore, the products produced by the present methods do not produce an amount of noxious odors that would be objectionable. The noxious odors are not necessarily non-detectable.

Disinfection is the destruction of pathogens, i.e., disease causing microorganisms, to some quantitative level.

The term "stabilization" is used in two ways in the present application. It relates to the ability of a process to maintain levels of disinfection by preventing pathogen regrowth. In this regard, the term "stable" relate to biological, chemical and/or physical stability. Biological stability means that indigenous microflora are able to successfully compete with pathogens and odor-causing microorganisms for nutrients. Chemical stability means that a chemical environment is created that is toxic to pathogens and odor-causing microorganisms. Physical stability means that physical conditions are created (e.g., low moisture content) that inhibit the survival or growth of pathogens or odor-causing microorganisms. The term "stabilization" also relates to the ability of a process to reduce odors and to prevent odor redevelopment.

The term "residual heat" as used herein in reference to a mineral by-product, refers to heat present in the mineral by-product at the time the mineral by-product is recovered in a hot state from the source thereof. Thus, the residual heat in the mineral by-product arises from heat employed in the processes that generate the mineral by-product. For example, the combustion of coal is conducted at very elevated temperatures and results in the production of hot fly ash. The fly ash will typically have a temperature of greater than about 400° F. to about 800° F. or higher. Thus, hot fly ash, recovered from hot exhaust gas stacks in, e.g., a coal-fired electrical generating facility, will have a large amount of residual heat that is useful in the processes in accordance with the present invention. A hot mineral by-product having residual heat therein, depending on the source of the mineral by-product, will typically have a temperature of from about 100° F. to about 1000° F. Similar temperature ranges may be expected for other hot mineral by-products useful in the present invention such as cement kiln dust, steel slag, and wood ash.

Intimate mixing includes thoroughly mixing organic waste and mineral by-product(s), preferably, in a mixer or blender until the mix is substantially homogeneous. Suitable mixers or blenders for this purpose would be known to those skilled in the art having read the present disclosure.

The present invention also relates to methods of producing stable, bio-mineral products that are preferably granular, which includes mixing, heating and drying, as set forth herein.

The present invention utilizes the unique properties of mineral by-products, when mixed with organic wastes, for heating, drying, odor absorption and granulation of the organic wastes. Accordingly, the present invention also provides granular bio-mineral products prepared by the methods of the present invention, and fertilizers, soil amendments and soil substitutes that include one or more of these granular bio-mineral products.

The present invention involves true enhanced organic waste drying with a combination of mineral by-products and heat drying, which is very different from methods previously used, which included for example a mere increase in solids content obtained by mixing wet sludge cake (15 to 35% solids) with totally dry mineral by-products and then drying by aeration.

The time-temperature relationship used by EPA for Class A disinfection has been well documented in practice. Similar relationships have been reported for Salmonella and enterovirus (EPA, 1999). The time-temperature relationship has embodied in it the physical nature of dewatered sewage sludge and the thermal conductivity of organic materials, such as sewage sludge. Because dewatered sludge exists as a heterogeneous mass, the time-temperature relationship must be conservative enough to ensure that all of the sludge is heated to the appropriate temperature for the appropriate time.

Mineral by-products used in the present invention may reduce the time-temperature requirement by producing an intimate mixture with the sludge. Organic waste, such as sludge, tends to occur in large clumps that stay together when dried, whereas the mineral by-products used in the present invention are fine-grained, high surface area mineral by-products. The intimate mixture of the sludge and mineral by-product breaks the sludge up into smaller particles and provides a large surface area contact between the sludge and mineral by-products. Mineral by-products, such as cement kiln dusts and fly ashes for example, have thermal conductivities that are as much as 10 times higher than that of organic materials like sludge. Intimately mixing fine-grained mineral by-product(s) provides the maximum surface to surface interaction between the by-product(s) and the sludge, which ensures that heat is efficiently transferred from the heated air in the dryer to the sludge, and results in the enhanced heating, sludge drying and disinfection of the present invention.

The organic waste of the present invention, may be in the form of a filter cake, which preferably contains between about 14 and about 40% solids. A significant portion of the water is held between organic waste particles. Alternatively, organic waste may be in the form of a moist feed that may, as a practical matter include from about 5% by weight to about 50% or more of solids. Preferably the organic waste is at least partially de-watered, that is, having a water content of less than about 95%, before mixing. When the organic waste is mixed with high surface area mineral by-products, the sludge water is dispersed throughout the mixture, increasing evaporative surfaces for water and aiding in drying.

Non-limiting examples of organic waste that may be disinfected and stabilized according to this invention include, but are not limited to, sewage sludges, biosolids (which include stabilized sewage sludge), animal manures, pulp and paper wastes, food waste, and other industrial waste such as fermentation biomass and pharmaceutical waste, and combinations thereof.

The mineral by-products in the present invention increase the efficiency of sludge heating and drying, thereby decreasing the time-temperature combination required for sludge disinfection and permitting the survival of beneficial microorganisms. The mineral by-products also create stabilizing conditions in the dried organic waste at pHs less than about 9 such that noxious odors are not produced if the dried material is rewetted. Noxious odors result for example, from the production of ammonia or methyl amines.

In particular, mineral by-products are used to greatly enhance thermal conductivity of the organic waste/mineral mixture and to form a more intimate contact between the heated mineral matter and the individual sludge particles, thereby permitting lower time-temperature combinations than required by the known methods for disinfection. Therefore, an embodiment of the present invention is the utilization of the physical and thermal properties of mineral by-products to better ensure that sludge particles are appropriately heated and to achieve pasteurization at time-temperature combinations below the time-temperature relationship required by EPA. This lower temperature and/or time is advantageous in that the beneficial microorganisms are not destroyed to the same extent that they would be in the drying methods previously used. In particular, the present invention preferably allows non-pathogenic microflora to survive. Therefore, according to this embodiment, the stable, granular bio-mineral product contains a non-pathogenic microflora. The indigenous microflora surviving this optimized process are able to repopulate over time.

The mineral by-products are preferably present in a sufficient amount to raise the total solids level of the mixture of organic waste and one or more mineral by-products to a predetermined minimum level. The minimum level of solids is preferably in the range from about 30% to about 50% by weight of the mixture.

Mineral by-products used in accordance with the present invention include those that result in a mixture of organic wastes and mineral by-products having a pH of less than about 9, preferably between about 7 and about 9. Preferred mineral by-products of the present invention have a pH of less than about 9 or mixtures of mineral by-products have a pH of less than about 9. Even more preferably, mineral by-products or mixtures thereof have a pH of between about 7 and about 9. The mineral by-products of the present invention preferably include those that will maintain pH of the final product below 9, thereby minimizing production of odor-causing gases that include ammonia and methyl amines. In the present invention, a novel combination of stabilizing forces arising from drying sludge with mineral by-products without having to maintain high pH is described. The stabilizing forces include sorption of biodegradable organics to mineral surfaces and protection from microorganisms in pores created by the bio-mineral mixture; high solids; air-filled porosity; a stable population of non-pathogenic microorganisms; and high soluble salts. Thus, the combination of the organic waste and a mineral by-product creates a physical, chemical and biological environment that inhibits the growth and survival of pathogens and odor-causing microorganisms.

Non-limiting examples of mineral by-products that may be used in accordance with the present invention include, but are not limited to, coal combustion wastes, calcitic and dolomitic limestone, cement kiln dust, rock fines including sand and gravel fines, gypsum, and steel slag. Other examples of mineral by-products that may be used include wood ash and mineral fines, as long as they are non-alkaline.

Coal combustion wastes include for example, fly ash. Fly ashes have variable fineness, solids content, and chemical composition. Fly ash is generally obtained from the combustion products of pulverized coal, usually by electrostatic precipitation. The chemical composition of ash depends on the type of coal that is burned. Typically, fly ash is made up of silica, alumina, iron oxide, calcium oxide, sulfur oxide and other trace materials. Coals from the western U.S. are typically high in calcium and thus, may contain a higher lime content than coals from the eastern U.S. Eastern coals are often higher in pyrite ($FeS_2$), which oxidizes on burning to $SO_2$, producing an acidic fly ash. Fly ashes are high in silicon, and are often in the form of a spherical glass. Some fly ashes are high in residual carbon in the form of charcoal and these are particularly effective in absorbing biosolids odors.

Fly ash is typically recovered from the hot exhaust gases of a coal-fired electrical generating plant. The temperature of the fly ash in such exhaust gases can reach as high as several hundred degrees Fahrenheit or higher. Consequently, the fly ash in such exhaust gases contains a large amount of residual heat. In accordance with some embodiments of the present invention, the residual heat in this hot fly ash is utilized to provide at least a portion of the heat for heating, drying, disinfecting and/or stabilizing the mixture of mineral by-products and organic waste.

Cement kiln dust is wasted in cement manufacture because soluble sodium and potassium salts in the cement kiln dust lower cement quality. Cement kiln dust is fine-grained, has high surface area, and is extremely dry. The composition is a function of the limestone and clay that are mixed and fired in a kiln to produce cement. Limestone may be primarily calcite ($CaCO_3$) or dolomite ($CaMg(CO_3)_2$), while clay may contain iron and aluminum oxides, silica ($SiO_2$), or kaolinite, mica, vermiculite or montmorillonite. Part of the limestone is calcined to form CaO and MgO, so that cement kiln dust contains a mixture of calcium and magnesium oxides and carbonates. Residual heat in the cement kiln dust may also be used to provide at least a portion of the heat for heating, drying, disinfecting and/or stabilizing the mixture of mineral by-products and organic waste.

Gypsum is a natural mineral that may used as a soil additive and in the manufacture of wall board. Synthetic gypsum, anhydrite ($CaSO_4$), and $CaSO_3$ have similar characteristics and are formed from the chemical reaction of $SO_2$ with lime in the flue of coal-fired power plants. Synthetic gypsum is used primarily for wall board manufacture.

Lime, also known as quicklime has the chemical composition CaO and is formed from the high-temperature calcining of limestone. Lime has a myriad of commercial uses that are based on the production of heat when lime reacts with water, and on its inherently high pH (~12.5). Limestone, in the form of calcite or dolomite, is one of the most abundant minerals in the earth's crust. It is widely used in agriculture to neutralize soil acidity; it is a precursor to lime production; and it is used in cement manufacture.

Mineral and rock fines is a general term relating to fine-grained residual materials from rock crushing and screening. These materials are often so fine-grained as to be too difficult to use in commercial applications and so become waste products. Examples of rock fines include those from limestone, feldspar, sand, gravel, granite and marble quarries.

Steel slag is a by-product of the smelting of iron ore. It contains additives such as limestone and the mineral constituents of the iron ore not recovered as molten iron. Residual heat in steel slag may also be used to provide at least a portion of the heat for heating, drying, disinfecting and/or stabilizing the mixture of mineral by-products and organic waste.

Wood ash results when wood is burned for example, as a fuel for steam and power production. The ash is a combination of mineral residue and charcoal. Wood ash has acid to alkaline pHs, and may be high in potassium. Depending on the wood type, wood ash may contain some reactive oxides that produce heat when wetted. Most wood ash is handled as a slurry, but dry ash is available. Residual heat in wood ash may also be used to provide at least a portion of the heat for heating, drying, disinfecting and/or stabilizing the mixture of mineral by-products and organic waste.

Non-limiting examples of preferred non-alkaline mineral by-products include fly ash, and other coal combustion by-products. In some preferred embodiments, residual heat in the fly ash or other coal combustion by-products is used to provide at least a portion of the heat for heating, drying, disinfecting and/or stabilizing the mixture of mineral by-products and organic waste.

When organic waste is mixed with one or more mineral by-products, and heated and dried (as described herein) for the purpose of disinfection, the resulting bio-mineral product is a stabilized organic waste product that is preferably granular, has a soil-like odor, and has a microbial population that facilitates odor control, exhibits long term stability, is resistant to pathogen regrowth and has increased value as a fertilizer. The product preferably contains at least about 60% solids and at least 20% by wet weight of the organic waste, and has a pH of less than about 9. The product preferably has odor characteristics that are less offensive than those of biosolids obtained by other methods. When the mineral byproduct-treated organic waste is rewetted to simulate the impact of rainfall in field storage, the wet material has superior odor characteristics as compared to those of the heated and dried biosolids itself.

According to a preferred embodiment of the present invention, sludge containing 14 to 40% solids is intimately mixed in a mixer with about 1% to about 20% by wet weight of mineral by-products, preferably about 5% to about 15%, most preferably about 10% to about 14%. According to one embodiment, the mineral by-product is fly ash present in an amount of at least 10% by wet weight of mineral by-products. Preferably the mineral by-products are selected such that after the sludge is mixed with mineral by-products, the mixture leaving the mixer has a pH of about 8 and the solids content is at least about 35% by weight. The mixture is then heated and dried in a dryer, preferably a rotary drum dryer, with hot air such that the resulting product has a solids content of about 60% or greater, is pathogen free, granular, biologically stable and has a pH of less than about 9.

In some embodiments of the present invention, the sludge is mixed directly with hot fly ash generated as a coal combustion by-product. The residual heat in the hot fly ash is then transferred to the sludge/fly ash mixture. The residual heat in the hot fly ash can reduce or even eliminate the amount of heat required in subsequent heating and/or drying steps. In any event, the residual heat in the hot fly ash, or other hot mineral by-product such as cement kiln dust, steel slag or wood ash is used to provide at least a portion of the heat for heating, drying, disinfecting and/or stabilizing the mixture of mineral by-products and organic waste.

The process of the present invention includes heating and drying the organic waste and mineral by-product mixture to form a stable, granular bio-mineral product. Preferably, the mixture is dried to at least about 60%, preferably at least about 90% solids, more preferably at least about 95% solids, most preferably as near 100% solids as possible.

The drying of a moist feed of organic waste, may be accomplished in a number of different ways by different types of devices. One such device is a pug mill; another is a rotating drum; a third is a simple covered mixing tank provided with stirring or agitating means. A fluidized bed is another example of an apparatus that may be used to dry the moist feed.

Additionally, commercial dryers, may be used alone or in combination with the pug mill or other drying methods, to dry the organic waste, or mixture of organic waste and mineral by-products. Such commercial dryers are available in two forms, direct and indirect. A dryer according to the present invention may include one or more direct dryers or indirect dryers.

Direct dryers bring heated air into direct contact with the organic waste. According to one embodiment of the present invention, exhaust stack gases from a power plant for example, may be used directly or waste steam or hot water from a power plant may be used with a heat exchanger to heat air for drying the organic waste.

Alternatively, indirect dryers may be used, which heat metal surfaces that come in contact with the organic waste. In one example of this embodiment, waste steam or hot water from a power plant may be used to heat the drying surfaces via a heat exchanger in which the waste steam or water is used to heat oil, the fluid normally used in indirect dryers.

Where residual heat from a mineral by-product such as hot fly ash is used to provide at least a portion of the heat for drying the moist feed of organic waste, the hot fly ash or other hot mineral by-product, or mixtures thereof, can be directly added to the drying device containing the moist organic waste. In such embodiments, the residual heat in the hot fly ash or other mineral by-product is transferred directly to the moist organic waste. Additionally, any of the mixing, heating and/or drying devices can be provided with means for indirectly transferring the residual heat in the hot fly ash or other mineral by-product to such device. For example, the residual heat in the hot fly ash can be used to heat a heat transfer fluid such as an oil. The hot oil would then transfer heat obtained from the hot mineral by-product indirectly to the moist organic waste, such as by contact with a heat exchange surface in contact with the organic waste. The hot fly ash could also be used as the heat transfer medium itself. For example, the moist organic waste could be indirectly heated by contact with a heat exchange surface that is itself heated by direct contact with the hot fly ash or other mineral by-product containing residual heat. In such embodiments, the cooled fly ash or other mineral by-product, i.e., after transferring a substantial amount of its residual heat either directly or indirectly to the heating and/or drying apparatus, may then be mixed in a cooled state with the organic waste in accordance with the present invention.

In embodiments where the residual heat of the hot fly ash or other mineral by-product is used to provide at least a portion of the heat for the drying and/or heating processes, a system for disinfecting and stabilizing organic waste in accordance with certain embodiments of the present invention may beneficially be located at or near the site where the hot mineral by-product is generated. For example, a system for disinfecting and stabilizing organic waste in accordance with the present invention could be located at the site of a coal-fired electrical generating plant which would provide a readily available source of hot fly ash for use in conjunction with the processes of the present invention. The hot fly ash could be transported, for example, from the hot exhaust gas stack, through insulated piping or other conduits, to any of the mixing, heating and/or drying components of the apparatus of the present invention.

Where the system for disinfecting and stabilizing organic waste in accordance with the present invention is not located at the site where the fly ash or other hot mineral by-product is generated, the fly ash or mineral by-product could be transported to the site of waste treatment by any means that would retain a substantial amount of the residual heat therein. For example, the hot fly ash could be transported via insulated transport equipment, such as a vehicle, to the site of waste treatment.

Non-limiting examples of suitable dryers according to the present invention include direct concurrent flow dryers, direct rotary dryers, concurrent forced air rotary dryers, horizontal single, double and triple pass indirect dryers, and vertical counter flow rotating disk indirect dryers.

Heat for heating and drying the mixture may alternatively, or additionally come from a source other than a power plant, such as a steam turbine or other sources known to those skilled in the art.

Depending on the organic waste being treated and the amount and type of feed and the degree of solids therein, multiple drying steps may be required in order to produce organic waste solids in accordance with the methods of the present invention, including the drying methods set forth herein. Heating and drying steps may take place before the organic waste solids are mixed with the one or more mineral by-products, during mixing with a hot mineral by-product such as hot fly ash that provides at least a portion of the heat required for heating and/or drying, or after mixing the mineral by-product with the organic waste solids. In some preferred embodiments, at least one heating step and at least one drying step occur after mixing. Such embodiments employing an additional heating and/or drying step are important when all of the heat necessary for heating, drying, disinfecting and/or stabilizing the organic waste is not supplied from residual heat in the mineral by-product. However, where the residual heat in the hot fly ash or other hot mineral by-product is sufficient to effect heating, drying, disinfecting and/or stabilization, it may then be unnecessary to subject the mixture to additional heating and/or drying procedures.

In the methods of the present invention, two or more steps may be performed concurrently with one another. For example, intimate mixing may take place concurrently with heating. For example, mixing hot fly ash or other hot mineral by-product directly with the organic waste may effect both mixing and heating steps concomitantly. Another example includes drying concurrently with heating, or drying then heating without transferring the mixture to a separate apparatus. Any of such drying and/or heating steps may utilize residual heat obtained from hot fly ash or other hot mineral by-product. In such embodiments, the residual heat may be transferred directly, such as by direct mixing of the hot mineral by-product with the organic waste, or indirectly, such as through a heat exchange surface, to the mixture in the heating and/or drying equipment.

The present invention also provides a system for disinfecting and stabilizing organic waste, which includes means for intimately mixing organic waste and one or more mineral by-products, heating means for heating the mixture of one or more mineral by-products and organic waste, and drying means for drying the mixture of organic waste and mineral by-product to produce a stable, granular bio-mineral product. The heating and or drying means may be provided with means for the direct or indirect transfer of residual heat from hot fly ash or other hot mineral by-product to the organic waste as described hereinabove. The organic waste, mineral by-product(s), and mixture thereof have a pH of less than about 9. In this embodiment, the mineral by-product(s) and organic waste are as described above with regard to the methods of the present invention., The means for intimately mixing the one or more mineral by-products with organic waste may include, for example, providing a mixer or blender as described in further detail with respect to the methods described above.

The heating means and drying means of this embodiment may be the same or different and may include for example, a pug mill or other non "dryer" apparatus described above, and/or one or more dryers described above and known to those skilled in the art, based on various factors including for example, the composition being dried, the amount of the composition being dried, and the extent to which it must be dried.

The present invention will now be described in detail with respect to showing how certain specific representative embodiments thereof may be made, the materials, apparatus and process steps being understood as examples that are intended to be illustrative only. In particular, the invention is not intended to be limited to the methods, materials, conditions, process parameters, apparatus and the like specifically recited herein.

EXAMPLES

Example 1

Figure 1:
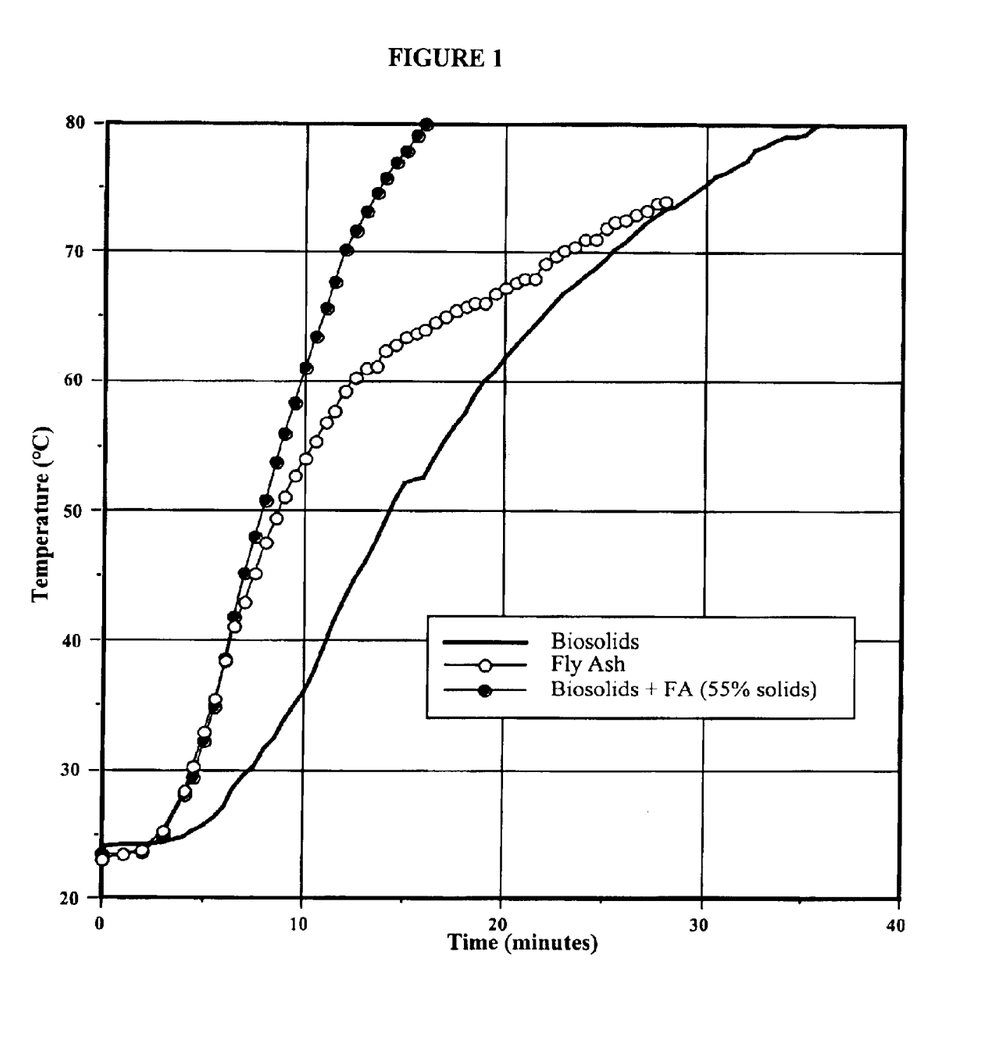
FIG. 1 is a graph showing the rate of heating biosolids, fly ash and a combination thereof.

The rate of heating of sludge with or without mineral byproduct was studied. Studies were conducted by mixing sewage sludge from the City of Toledo, Ohio (Bayview) with various amounts of fly ash (dead ash–no temperature rise/pH<9), immersing centrifuge tubes containing the materials in a 90° C. water bath, and monitoring the temperatures of the various mixtures over time. The results are shown in FIG. 1. FIG. 1 shows that sludge mixed with fly ash heats faster than biosolids alone or fly ash alone.

The faster heating rate of fly ash alone compared to sludge alone may be attributed to the higher thermal conductivity of the fly ash compared to sludge and the water in the sludge. The unexpected finding that the sludge-fly ash mixtures heated faster than fly ash may be due to the granular nature of the sludge-fly ash mixture, thereby producing greater surface area for the solids to contact the hot air. The more rapid heating of the sludge-fly ash mixture than sludge alone will permit heating of sludge to disinfecting temperatures more rapidly than in a conventional sludge dryer.

Figure 2:
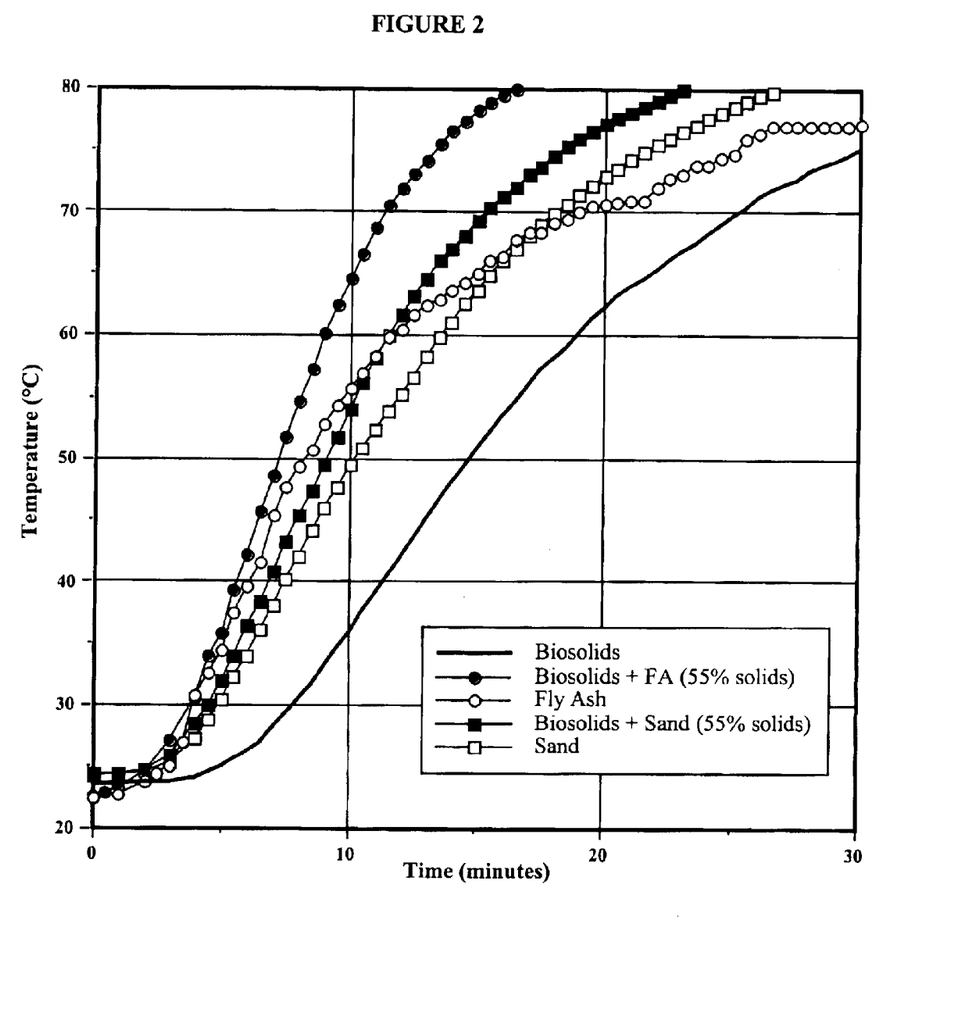
FIG. 2 is a graph showing the rate of heating biosolids, fly ash, sand and combinations thereof.

FIG. 2 shows data for heating sludge with either fly ash or sand. FIG. 2 shows that biosolids mixed with fly ash or biosolids mixed with sand heated faster than biosolids alone, fly ash alone or sand alone. Fly ash enhanced heating more than sand. Both mineral materials increased rate of heating faster than sludge alone or either fly ash or sand alone. This may be a result of the higher surface area of fly ash, the more granular mixture produced with fly ash, or it may be due to some undetermined physical-chemical reaction between fly ash and sludge. Sand is chemically inert compared to fly ash.

Example 2

The effect of fly ash on the efficiency of drying of sewage sludge was studied. Samples of anaerobically digested sewage sludge from Toledo, Ohio were mixed with varying percentages of coal fly ash and dried in a chamber for varying periods of time and temperatures. Water loss from sludge was monitored. Water loss was corrected for the dilution effect of the fly ash so that water loss was determined for amount of sludge.

Table 1 below shows that increasing doses of fly ash increased the extent of sludge drying. Air temperature also increased drying but to a lesser extent. Air temperature generally has little effect on drying if air flow rates are such that the air does not become water saturated. True enhanced sludge drying with a combination of mineral by-products and heat drying, as shown in the present invention, is very different from a mere increase in solids content obtained by mixing wet sludge cake (15 to 35% solids) with totally dry mineral by-products and then drying by aeration.

TABLE 1

Effect of fly ash on drying of sewage sludge.

| Test | Fly Ash (%) | Drying Time (min) | Max Temp in Chamber (C.) | Starting Solids (%) | Ending Solids (%) | g Water Removed/ 100 g sludge |
|---|---|---|---|---|---|---|
| 1 | 0% | 30 | NA* | 19.0% | 21.0% | 2.0 |
|   | 36% | 30 | NA | 38.7% | 39.7% | 1.4 |
|   | 46% | 30 | NA | 42.5% | 44.3% | 2.6 |
|   | 53% | 30 | NA | 46.8% | 47.8% | 1.5 |
|   | 66% | 30 | NA | 56.0% | 57.7% | 2.8 |
|   | 76% | 30 | NA | 58.8% | 61.7% | 5.1 |
| 2 | 0% | 60 | NA | 18.6% | 22.8% | 4.2 |
|   | 40% | 60 | NA | 41.2% | 92.0% | 71.0 |
| 3 | 0% | 30 | 63.6 | 18.6% | 23.1% | 4.5 |
|   | 10% | 30 | 67.8 | 26.2% | 32.0% | 6.5 |
|   | 20% | 30 | 53.9 | 32.4% | 39.9% | 9.0 |
|   | 30% | 30 | 43.4 | 38.0% | 52.5% | 18.9 |
|   | 40% | 30 | 47.2 | 41.2% | 55.3% | 19.7 |
| 4 | 0% | 30 | 55.9 | 18.6% | 20.3% | 1.7 |
|   | 10% | 30 | 43.8 | 26.2% | 30.8% | 5.1 |
|   | 20% | 30 | 45.9 | 32.4% | 38.1% | 6.8 |
|   | 30% | 30 | 47.4 | 38.0% | 44.2% | 8.1 |
|   | 40% | 30 | 47.8 | 41.2% | 47.5% | 8.8 |
| 5 | 0% | 30 | 77.7 | 18.6% | 23.3% | 4.8 |
|   | 10% | 30 | 103.3 | 26.2% | 33.4% | 7.9 |
|   | 20% | 30 | 84.2 | 32.4% | 41.6% | 11.0 |
|   | 30% | 30 | 71.5 | 38.0% | 45.2% | 9.3 |
|   | 40% | 30 | 69.4 | 41.2% | 54.7% | 18.8 |
| 6 | 30% | 60 | 49.9 | 38.0% | 49.0% | 14.3 |
| 7 | 0% | 64 | 64.1 | 18.6% | 30.7% | 12.1 |
|   | 30% | 30 | 59.3 | 38.0% | 42.1% | 5.4 |
|   | 30% | 60 | 58.4 | 38.0% | 54.8% | 21.8 |
|   | 30% | 84 | 64.1 | 38.0% | 82.9% | 58.4 |

*Not measured

Example 3

Non-alkaline fly ash from Wyandotte, Mich. was mixed at a 30% dose (wet weight of sludge) to raw sludge from Monroe, Mich. The mixture was placed in a drying chamber (see Example 2) for 1 hour. Samples of the dried mixtures were then placed in glass tubes in a 70° C. water bath. The tubes were removed from the water bath at various time intervals and the contents were assayed for the presence of fecal streptococci by standard methods. The temperature of the dried mixture in the tube in the water bath was also recorded. The experimental process was duplicated for sewage sludge without fly ash addition.

Table 2 below shows that complete destruction of fecal streptococci occurred at 10 minutes in the fly ash-treated sludge, while low but still positive values were observed in the untreated sludge samples even after 30 minutes, as shown in Table 3. The enhanced rate of disinfection may be attributed to the more rapid rate of heating when sludge is mixed with fly ash as previously shown in Example 1.

TABLE 2

Effect of fly ash in conjunction with heating and drying on destruction of fecal streptococci bacteria in raw sewage sludge.

| Sample | % Solids pre-Dry | % Solids post-Dry | g Water Removed/100 | Max Temp in Dryer (° C.) |
|---|---|---|---|---|
| Biosolids + FA | 40.2% | 57.8% | 17.6 | 40.5 |

| Biolsolids + FA Time/Incubation | Fecal Strep post-Dry (MPN/gDWS) Total DWS | Fecal Strep post-Dry (MPN/gDWS) Biolsolids DWS | Temp in Bath (° C.) |
|---|---|---|---|
| T0 @ 70° C. | 1.0E + 08 | 2.2E + 08 | 36 |
| T5 @ 70° C. | 6.4E + 05 | 1.4E + 06 | 50.2 |
| T10 @ 70° C. | <2.1E + 00 | <4.5E + 00 | 62.6 |
| T20 @ 70° C. | <2.1E + 00 | <4.5E + 00 | 68.6 |
| T30 @ 70° C. | <2.1E + 00 | <4.5E + 00 | 69.8 |

Table 3 shows that the untreated sludge sample had a temperature of 57.7° C. at 10 minutes, while the sludge and fly ash mixture from Table 2 had a temperature of 62.6° C. at 10 minutes. In addition, chemical characteristics of fly ash, such as high soluble salts, increase the effectiveness of disinfection. This may be seen in Table 3 where complete disinfection was achieved at 30 minutes with fly ash while detectable fecal streptococci were still present in sludge alone at 30 minutes, even though both samples had the same temperature (69.7 vs. 69.8° C.).

TABLE 3

Effect of fly ash in conjunction with heating and drying on destruction of fecal streptococci bacteria in raw sewage sludge.

| Sample | % Solids pre-Dry | % Solids post-Dry | g Water Removed/100 | Max Temp in Dryer (° C.) |
|---|---|---|---|---|
| Biosolids | 25.8% | 29.9% | 4.1 | 54.2 |

| Biosolids Time/Incubation | Fecal Strep post-Dry (MPN/gDWS) | Temp in Bath (° C.) |
|---|---|---|
| T0 @ 70° C. | 4.5E + 07 | 27.2 |
| T5 @ 70° C. | >1.5E + 07 | 44.3 |
| T10 @ 70° C. | 5.8E + 04 | 57.7 |
| T20 @ 70° C. | 4.0E + 00 | 67.4 |
| T30 @ 70° C. | 4.0E + 00 | 69.7 |

Example 4

Figure 3:
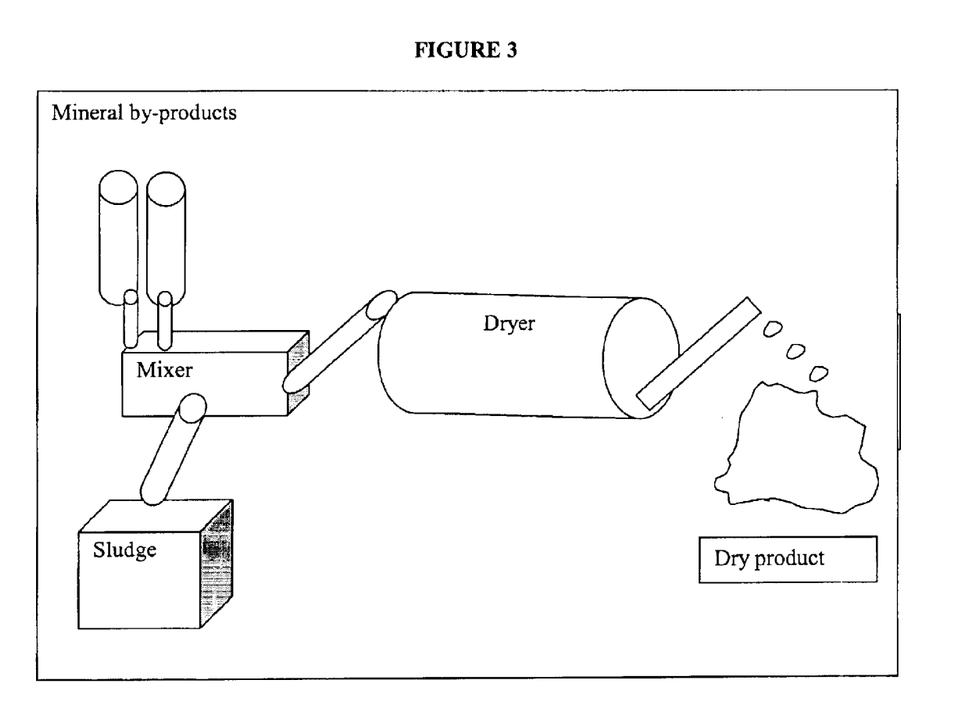
FIG. 3 is an example of a system according to the present invention, in which methods according to the present invention may be performed.

FIG. 3 shows a system according to the present invention, in which methods according to the present invention may be performed. A dewatered sludge or other organic waste, containing about 14 to 40% solids, is mixed with fly ash having a pH of about 8 in a high-speed screw auger or pug mill mixer. The amount of fly ash added to the sludge is at least about 10% on a wet sludge weight basis. The mixture leaving the mixer has a solids content of at least about 35%. The pH of the mixture is less than 9. The mixture is introduced into a single-pass rotary kiln dryer equipped with an intake for heated air, a hopper to introduce the mixture, vanes in the dryer drum to agitate the product, a discharge hopper and conveyor to remove the product and transfer it to storage, and a venturi and scrubber system to remove particulates and gaseous emissions. The air temperature and air flow in the dryer are controlled to give the required product temperature, retention time and final product solids. The final product is pathogen free, granular and biologically stable, has a solids content of 60% or greater, a pH of less than 9, is disinfected to EPA Class A standards, and will not generate noxious odors when rewetted.

Example 5

A partially dewatered wastewater sludge was treated by a process according to the present invention, of treating and stabilizing sludges so that it achieves the U.S. Environmental Protection Agency's Class A standard for pathogen reduction, by intimately mixing sludge containing about 20% solids with over about 10% by wet weight of fly ash having a pH of about 8. The mixture leaving the mixer had a solids content of at least about 35% and a pH less than 9. The mixture was then heated and dried in a rotary drum dryer with hot air such that the resulting product had solids content of about 60%. The resulting product was a biologically stable, granular bio-mineral product.

While the present invention is described with respect to particular examples and preferred embodiments, it is understood that the present invention is not limited to these examples and embodiments. In particular, the present invention is not limited to use with particular organic waste or particular mineral by-products. Moreover, the present invention is not limited to use with the particular exemplified dryers or drying conditions, mixers or mixing conditions or heaters or heating conditions. Additionally, further ingredients may be added to the organic waste and mineral by-products before or after mixing so long as the pH of the mixture is maintained below about 9.

The present invention as claimed therefore, includes variations from the particular examples and preferred embodiments described herein, as will be apparent to one of skill in the art.

We claim:

1. A method of disinfecting and stabilizing organic waste, comprising
    intimately mixing organic waste with one or more mineral by-products to form a mixture having a pH of less than about 9; and
    heating and drying the mixture to produce a stable, granular bio-mineral product, wherein at least a portion of the heat for heating and/or drying the mixture is provided by residual heat in the mineral by-product and, wherein the pH is maintained at less than about 9 throughout the method.

2. The method of claim 1, wherein the mineral by-product is selected from the group consisting of coal combustion waste, cement kiln dust, steel slag, wood ash and combinations thereof.

3. The method of claim 2, wherein the coal combustion waste comprises hot fly ash.

4. The method of claim 1, comprising directly transferring residual heat from the mineral by-product to the organic waste.

5. The method of claim 4, wherein residual heat from the mineral by-product is directly transferred to the organic waste by mixing a hot mineral by-product with the organic waste.

6. The method of claim 1, comprising indirectly transferring residual heat from the mineral by-product to the organic waste.

7. The method of claim 6, wherein residual heat from the mineral by-product is indirectly transferred to the organic waste by contacting a hot mineral by-product with a heat exchange surface in contact with the organic waste.

8. The method of claim 1, wherein the organic waste is partially de-watered.

9. The method of claim 1, wherein the one or more mineral by products are present in an amount of at least about 10% by wet weight of the organic waste.

10. The method of claim 1, wherein the organic waste comprises waste selected from the group consisting of sewage sludge, animal manure, bio solid, pulp and paper waste, fermentation biomass, food waste, and combinations thereof.

11. The method of claim 1, wherein the one or more mineral by-products comprise a mineral by-product having a pH of less than about 9 or a mixture of mineral by-products having a combined pH of less than about 9.

12. The method of claim 1, wherein the one or more mineral by-products comprise two or more mineral by-products, at least one of which has residual heat.

13. The method of claim 12, wherein one or more mineral by-products is selected from the group consisting of coal combustion wastes, wood ash, calcitic and dolomitic limestone, cement kiln dust, mineral and rock fines, gypsum, steel slag, and combinations thereof.

14. The method of claim 1, wherein the level of solids in the mixture is in the range from about 30% to about 50% by weight of the mixture.

15. The method of claim 1, wherein the heating and drying takes place in a hot air dryer.

16. The method of claim 1, wherein the heating and drying is by a direct or indirect dryer.

17. The method of claim 1, wherein the stable, granular bio-mineral product is disinfected.

18. The method of claim 1, wherein the stable, granular bio-mineral product has a solids level of at least about 60% after drying.

19. The method of claim 1, wherein the stable, granular bio-mineral product has a pH less than about 9 after drying.

20. A method of making a stable, granular bio-mineral material, comprising intimately mixing organic waste with one or more mineral by-products to form a mixture; and heating and drying the mixture to produce a stable, granular bio-mineral product, wherein at least a portion of the heat for heating and/or drying the mixture is provided by residual heat in at least one of the one or more mineral by-products; and wherein the mixture has a pH of less than about 9 and, wherein the pH is maintained at less than about 9 throughout the method.

21. A stable, granular bio-mineral product made by a method comprising intimately mixing organic waste with one or more mineral by-products to form a mixture having a pH of less than about 9; and heating and drying the mixture to produce a stable, granular bio-mineral product, wherein at least a portion of the heat for heating and/or drying the mixture is provided by residual heat in at least one of the one or more mineral by-products and, wherein the pH is maintained at less than about 9 throughout the method.

22. A fertilizer comprising a biologically stable, granular bio-mineral product made by a method comprising intimately mixing organic waste with one or more mineral by-products to form a mixture having a pH of less than about 9; and heating and drying the mixture to produce a stable, granular bio-mineral product, wherein at least a portion of the heat for heating and/or drying the mixture is provided by residual heat in at least one of the one or more mineral by-products and, wherein the pH is maintained at less than about 9 throughout the method.

23. A soil amendment comprising a biologically stable, granular bio-mineral product made by a method comprising intimately mixing organic waste with one or more mineral by-products to form a mixture having a pH of less than about 9; and heating and drying the mixture to produce a stable, granular bio-mineral product, wherein at least a portion of the heat for heating and/or drying the mixture is provided by residual heat in at least one of the one or more mineral by-products and, wherein the pH is maintained at less than about 9 throughout the method.

24. A soil substitute comprising a biologically stable, granular bio-mineral product made by a method comprising intimately mixing organic waste with one or more mineral by-products to form a mixture having a pH of less than about 9; and heating and drying the mixture to produce a stable, granular bio-mineral product, wherein at least a portion of the heat for heating and/or drying the mixture is provided by residual heat in at least one of the one or more mineral by-products and, wherein the pH is maintained at less than about 9 throughout the method.

* * * * *

UNITED STATES PATENT AND TRADEMARK OFFICE
CERTIFICATE OF CORRECTION

PATENT NO. : 6,752,849 B2
DATED : June 22, 2004
INVENTOR(S) : Logan et al.

It is certified that error appears in the above-identified patent and that said Letters Patent is hereby corrected as shown below:

<u>Column 13,</u>
Lines 27 and 29, change "Biolsolids" to -- Biosolids --.

Signed and Sealed this

Twenty-fourth Day of May, 2005

JON W. DUDAS
*Director of the United States Patent and Trademark Office*